United States Patent [19]

Holy et al.

[11] Patent Number: 4,659,825

[45] Date of Patent: Apr. 21, 1987

[54] ISOMERIC O-PHOSPHONYLMETHYL DERIVATIVES OF ENANTIOMERIC AND RACEMIC 9-(2,3-DIHYDROXYPROPYL)ADENINE

[75] Inventors: Antonin Holy; Ivan Rosenberg; Karel Slama, all of Prague, Czechoslovakia

[73] Assignee: Ceskoslovenska akademie, Czechoslovakia

[21] Appl. No.: 568,719

[22] Filed: Jan. 6, 1984

[30] Foreign Application Priority Data

Jan. 6, 1983 [CS] Czechoslovakia .................. 88-83

[51] Int. Cl.$^4$ .......................... C07F 9/38; C07F 9/65; C07H 19/16
[52] U.S. Cl. ............................ 544/244; 260/502.4 R; 536/27
[58] Field of Search ........................................ 544/244

[56] References Cited

U.S. PATENT DOCUMENTS 4,199,574  4/1980  Schaeffer ...................... 544/244 X

FOREIGN PATENT DOCUMENTS 3400278  7/1984  Fed. Rep. of Germany ...... 544/244
84/04748 12/1984  Int'l Pat. Institute .............. 544/244
0332727 11/1977  U.S.S.R. ............................. 544/244

OTHER PUBLICATIONS

Antonin Holy and Ivan Rosenberg "Preparation of 5'-O-Phosphonylmethyl Analogues of Nucleoside-5'-Phosphates, 5'-Diphosphates and 5'-Triphosphates" *Collection of Czechoslovak Chemical Communications*, vol. 47, 1982, pp. 3447-3463.

*Primary Examiner*—Mark L. Berch
*Assistant Examiner*—Diana G. Rivers
*Attorney, Agent, or Firm*—Leydig, Voit & Mayer

[57] ABSTRACT

This invention relates to isomeric O-phosphonylmethyl derivatives of the formula I

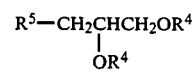

wherein $R^5$ designates an adenin-9-yl moiety, $R^4$ are alternately a hydrogen atom and a $-CH_2P(O)(OH)_2$ group, and the configuration at the carbon atom in the position 2 is S, R or RS.

The compounds according to the invention are biologically active as inhibitors of metabolic processes and in organism they are stable towards enzymes, cleaving phosphomonoester bonds.

The said compounds exhibit also chemosterilizing action on insects.

1 Claim, No Drawings

ISOMERIC O-PHOSPHONYLMETHYL DERIVATIVES OF ENANTIOMERIC AND RACEMIC 9-(2,3-DIHYDROXYPROPYL)ADENINE

This invention relates to isomeric O-phosphonylmethyl derivatives of enantiomeric and racemic vicinal diols and method of preparing them.

Esters of phosphoric acid are of key importance in processes occuring in the living matter. Isosteric analogues of these compounds can act as inhibitors of metabolic processes and show thus biological activity. One important condition for their practical use is their stability in organism, especially towards enzymes cleaving phosphomonoester bonds. This condition is fulfilled in the case of O-phosphonylmethyl derivatives of organic alcohols which in many respects resemble natural organophosphates. These compounds, however, contain a bond between the phosphorus and carbon atom, which is stable towards enzymes. Such derivatives were prepared by reaction of alkoxides with esters of chloromethanephosphonic acid (E. N. Walsh, T. M. Beck, A. D. F. Toy: J. Amer. Chem. Soc. 78, 4455 (1956)), by reaction of phosphorus trichloride with formals (U.S. Pat. No. 2 500 022) or by treatment of diesters of p-toluenesulfonyloxymethanephosphonic acid with sodium alkoxide (Author's Certificate No. 220,713 PV 4087-81). However, all these reactions require subsequent hydrolysis of phosphonic esters which proceeds only with difficulty.

This invention relates to isomeric O-phosphonylmethyl derivatives of the general formula I

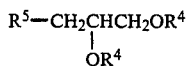

$$R^5-CH_2CHCH_2OR^4 \quad (I)$$
$$\mid$$
$$OR^4$$

wherein $R^5$ designates a adenin-9-yl moiety $R^4$ are alternately a hydrogen atom and a $-CH_2P(O)(OH)_2$ group, and the configuration at the carbon atom in the position 2 is S, R or RS.

The method of preparing compounds of formula I, wherein $R^5$ designates an adenin-9-yl moiety, is characterised in that enantiomeric or racemic compounds of the general formula V

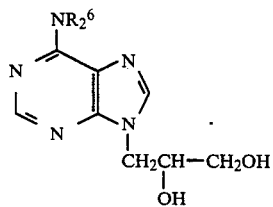

wherein $R^6$ designates a hydrogen atom or a $=CH-N(CH_3)_2$ group, are induced to enter into a reaction with 1-2 equivalents of chloromethanephosphonyl dichloride of the formula III

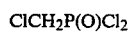

$$ClCH_2P(O)Cl_2 \quad (III)$$

and simultaneously with 2 equivalents (related to the compound III) of a tertiary base, preferably pyridine, in an aprotic organic solvent, preferably pyridine, at temperatures 0°-80° C., whereupon the reaction mixture is treated with an aqueous solution of an alkali metal hydroxide at temperatures 0°-100° C. and the compounds of the formula I are isolated by desalting, preferably by chromatography on a ion-exchange resin.

The reaction is in principle based on formation of monoester of chloromethanephosphonic acid which can be either isolated or without isolation converted by intramolecular cyclization reaction in a strongly alkaline medium directly into compounds of the general formula I.

Chloromethanephosphonyl dichloride of the formula III, required for the reaction, can be prepared preferably by reaction of phosphorus trichloride with paraformaldehyde (U.S. Pat. No. 2 874 184; M. I. Kabachnik, E. S. Shepeleva: Izv. Akad. Nauk SSSR, Ser. Chim. 1951, 185; R. L. McConnell, M. A. McCall, N. W. Coover: J. Org. Chem. 22, 462 (1957)), by reaction of chloromethanephosphonic or hydroxymethanephosphonic acid with thionyl chloride (R. A. B. Bannard, J. R. Gilpin, G. R. Vavasour, A. F. McKay; Can. J. Chem. 31, 976 (1953)), by reaction of methylene chloride with phosphorus trichloride in the presence of aluminium chloride (A. M. Kinnear, E. A. Perren: J. Chem. Soc. 1952, 3437), or by oxidation of chloromethyldichlorophosphine with nitrogen oxides (A. J. Jakubovich, V. A. Ginsburg: Zh. Obshch. Khim. 22, 1534 (1952)). The reaction proceeds equally well with bromomethanephosphonyl dibromide which is, however, less easily accessible than the compound of the formula III (J. A. Cade: J. Chem. Soc. 1959, 2272).

Hydrogen chloride, arising in the reaction of compounds of the formula II with the chloro derivative III, is bonded to a tertiary base (e.g. pyridine, its alkyl derivatives, or triethylamine). The reaction can be carried out either in an inert organic solvent (ether, dioxane or chlorinated hydrocarbons), the complete solution of the starting compounds being not necessary, or directly in pyridine. The reaction time is usually several hours at room temperature but the reaction can be carried out also at elevated temperatures. It can be performed in usual reactors, the only condition being use of dry reaction components and solvents and exclusion of moisture during the reaction with the compound III. After evaporation of the solvent, the mixture is treated with water and then with an aqueous alkali, such as lithium, sodium or potassium hydroxide in the final concentration 0.5-2.0 mol $l^{-1}$, at room temperature for 24 hours or at an elevated temperature for a shorter time, affording thus the final product of the general formula I. In order to enhance the solubility of the intermediates with hydrophobic groups it is advisable to use mixtures of the aqueous hydroxides with ethanol, methanol or dioxane keeping the same final hydroxide concentration as mentioned above. The use of lithium hydroxide in the workup of the reaction mixtures is very advantageous since the excess hydroxide can be removed either with a cation-exchange resin in an acid form or with hydrochloric acid with subsequent removal of the inorganic lithium salts by extraction with a mixture of acetone and ethanol.

The isomers of compounds of the formula I can be separated e.g. by chromatography on an ion-exchange resin.

In the form of free acids, some of the compounds of the formula II are sparingly soluble in water and it is therefore advantageous to convert them into their soluble lithium, sodium, potassium or ammonium salts.

Compounds of the general formula II have a chemosterilizing action on insects. This activity can be documented by bioassays for ovicidal activity which express inhibition of larval hatching from the eggs. The test animals were freshly emerged adults of *Pyrrhocoris apterus L.* and the tested compounds were administered as solutions in drinking water. The concentration 1 mg.ml$^{-1}$ corresponded to the dose of 1 mg/g/24 h. Each test was performed on a group of 10 males and 10 females and evaluated according to toxicity and hatchability of the eggs of the first and the second egg batches. The activity of the compounds of the formula I is documented by the data in Table I.

TABLE I

Inhibition of egg hatching in the first and second egg batch in *Pyrrhocoris apterus L.* after oral administration of the compounds of formula I to adults of both sexes (% inhibition, related to control eggs)

| Concentration (mg · ml$^{-1}$ of water) | 0.01 | 0.05 | 0.1 | 1.0 |
|---|---|---|---|---|
| 1 (RS)-I (R$^5$ = adenin-9-yl) | 30 | 50 | 100 | 100 |
| (2'-isomer) | — | — | 27 | — |
| (3'-isomer) | — | — | 61 | — |
| 3 (RS)-9-(2,3-dihydroxy-propyl)adenine (II, R$^6$ = H) (standard) | 0 | 10 | 37 | 100 |

This invention is illustrated by the following Examples of execution which do not mean any limitations to the invention.

EXAMPLE I

A mixture of 9-(RS)-(2,3-dihydroxypropyl)adenine (10 mmol), dimethylformamide (25 ml) and dimethylformamide dimethyl acetal (10 ml) is stirred in a stoppered flask at room temperature overnight. The solvent is evaporated at 40° C. and 13 Pa, the residue is coevaporated successively with 70% aqueous pyridine (50 ml) and pyridine (3×30 ml) and is dissolved in 1,2-dichloroethane (100 ml). Pyridine (3.5 ml), followed by chloromethanephosphonyl dichloride (3.34 g; 20 mmol) is added and the mixture is stirred in a stoppered flask overnight. A solution of triethylammonium hydrogen carbonate (0.2 mol.l$^{-1}$; 50 ml), pH 7.5, is added and after 2 hours the mixture is taken down at 40° C. under reduced pressure (water pump). The dry residue is codistilled with ethanol (3×100 ml), 50% acetic acid (100 ml) is added and the mixture is kept at 40° C. for 15 hours. After evaporation in vacuo, the residue is codistilled with water (3×50 ml), dissolved in water (50 ml) and the solution is applied on a column of Dowex 50×8 (H$^+$-form; 300 ml). The product is eluted with water, the pertinent fractions are taken down and the residue is precipitated with ether from methanolic solution to give 650 mg (20%) of the 3'-chloromethanephosphonyl derivative, 900 mg (28%) of the 2'-chloromethanephosphonyl derivative, and 750 mg (23.5%) of a mixture of both. Each of them (1 mmol) is heated with a solution of lithium hydroxide (2 mol.l$^{-1}$; 10 ml) to 70° C. for 8 hours, the mixture is neutralized with hydrochloric acid, taken down and the residue is treated with ethanol and acetone as described in Example 2. The yield of the isomerically pure compound or of the isomeric mixture (compounds of the formula I, R$^1$=adenin-9-yl) is 80–90% (as the dilithium salt). The compounds are isomerically pure (R$_F$= 0.18 in systems S1) and homogeneous according to HPLC on C18 silica gel.

EXAMPLE 2

Chloromethanephosphonyl dichloride (1.67 g) is added to a solution of 9-(S)-(2,3-dihydroxypropyl)adenine (1.05 g) in pyridine (50 ml) and the mixture is stirred in a stoppered flask at room temperature for 15 hours. After addition of water (10 ml) and evaporation of pyridine in vacuo, the dry residue is heated with a solution of lithium hydroxide (2 mol.l$^{-1}$; 50 ml) to 80° C. for 6 hours. The mixture is neutralized with hydrochloric acid and taken down in vacuo. The dry residue is dissolved in water (10 ml) and the solution is applied on a column of Dowex 50×8 (H$^+$-form; 150 ml). After washing with water (250 ml), the product is eluted with 2% ammonia (500 ml). The ammonia eluate is taken down in vacuo and the residue is dissolved in water (10 ml) and applied on a column of Dowex 1×2 (acetate; 100 ml). After washing with water, the product is eluted with a linear gradient of water (2 liters) and 0.5M acetic acid (2 liters). The UV-absorbing fraction of the product is taken down, the residue is codistilled with water (3×25 ml) and crystallized from water, affording a mixture of the stereoisomeric 2'(3')-O-phosphonylmethyl derivatives of 9-(S)-(2,3-dihydroxypropyl)adenine (compound of the formula I, R$^1$=adenin-9-yl) in 50–60% yield. The product is obtained in the form of the free acid and is homogeneous according to paper chromatography (R$_F$=0.18 in system S1) as well as HPLC on C18 silica gel.

What we claim is:

1. Isomeric O-phosphonymethyl derivatives of enantiomeric and racemic vicinal diols having the formula I

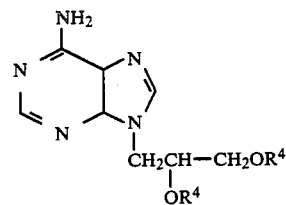

wherein one R$^4$ is a hydrogen atom and the other R$^4$ is a —CH$_2$P(O)(OH)$_2$ group, and the configuration at the carbon atom in the position 2 is R, S or RS.

* * * * *